US008989458B2

(12) United States Patent
Yamagishi et al.

(10) Patent No.: US 8,989,458 B2
(45) Date of Patent: Mar. 24, 2015

(54) IMAGE DIAGNOSIS SUPPORT SYSTEM AND IMAGE DIAGNOSIS SUPPORT METHOD

(75) Inventors: Hiromasa Yamagishi, Otawara (JP); Muneyasu Kazuno, Nasushiobara (JP); Kenichi Niwa, Otawara (JP); Takashi Masuzawa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 760 days.

(21) Appl. No.: 12/246,117

(22) Filed: Oct. 6, 2008

(65) Prior Publication Data
US 2009/0103790 A1 Apr. 23, 2009

(30) Foreign Application Priority Data
Oct. 17, 2007 (JP) ................................. 2007-270325

(51) Int. Cl.
*G06K 9/00* (2006.01)
*G06Q 10/00* (2012.01)
*G06Q 50/00* (2012.01)
*G06F 19/00* (2011.01)
*G06F 15/16* (2006.01)
(Continued)

(52) U.S. Cl.
CPC ............ *G06F 19/322* (2013.01); *G06F 19/321* (2013.01); *G06F 19/3487* (2013.01)
USPC ................... 382/128; 705/2; 705/3; 709/204; 709/217; 709/220; 709/223

(58) Field of Classification Search
None
See application file for complete search history.

(56) References Cited

U.S. PATENT DOCUMENTS

2001/0041991 A1* 11/2001 Segal et al. ........................ 705/3
2002/0169635 A1* 11/2002 Shillingburg ..................... 705/2
2004/0254763 A1* 12/2004 Sakai et al. .................. 702/184
(Continued)

FOREIGN PATENT DOCUMENTS

JP 2004-267273 9/2004
JP 2005-43951 2/2005
(Continued)

OTHER PUBLICATIONS

U.S. Appl. No. 12/100,780, filed Apr. 10, 2008, Muneyasu Kazuno, et al.
(Continued)

*Primary Examiner* — Amir Alavi
*Assistant Examiner* — Kenny Cese
(74) *Attorney, Agent, or Firm* — Oblon, McClelland, Maier & Neustadt, L.L.P.

(57) ABSTRACT

There is disclosed an image diagnosis support system which acquires a medical image from a medical image imaging unit, generates object information on the medical image, stores the medical image and the object information in a data storage unit and a database, stores case information for each patient based on the object information in correspondence with a case name and information of the medical image in an information table, collects the case information for each patient read from the information table in correspondence with the case name in accordance with a conference instruction and the medical image read from the data storage unit and the database in accordance with the information of the medical image, respectively, as conference information by a conference information display•feedback section to display the same, and feeds back a conference result based on display contents to the information table.

22 Claims, 13 Drawing Sheets

(51) Int. Cl.
*G06F 15/177* (2006.01)
*G06F 15/173* (2006.01)

(56) References Cited

U.S. PATENT DOCUMENTS

| | | |
|---|---|---|
| 2007/0238963 A1 | 10/2007 | Kaminaga et al. |
| 2008/0212854 A1 | 9/2008 | Fukatsu et al. |
| 2008/0256181 A1* | 10/2008 | Morita et al. ............... 709/204 |
| 2009/0028403 A1* | 1/2009 | Bar-Aviv et al. ............ 382/128 |
| 2011/0082794 A1* | 4/2011 | Blechman .................... 705/50 |

FOREIGN PATENT DOCUMENTS

| | | |
|---|---|---|
| JP | 2005-189915 | 7/2005 |
| JP | 2007-65862 | 3/2007 |
| JP | 2007-167634 | 7/2007 |

OTHER PUBLICATIONS

U.S. Appl. No. 12/061,340, filed Apr. 2, 2008, Kenichi Niwa, et al.
U.S. Appl. No. 12/174,055, filed Jul. 16, 2008, Satoru Ohishi, et al.
Japan Office Action issued Feb. 5, 2013, in Patent Application No. 2008-267616 (with English-language translation).

\* cited by examiner

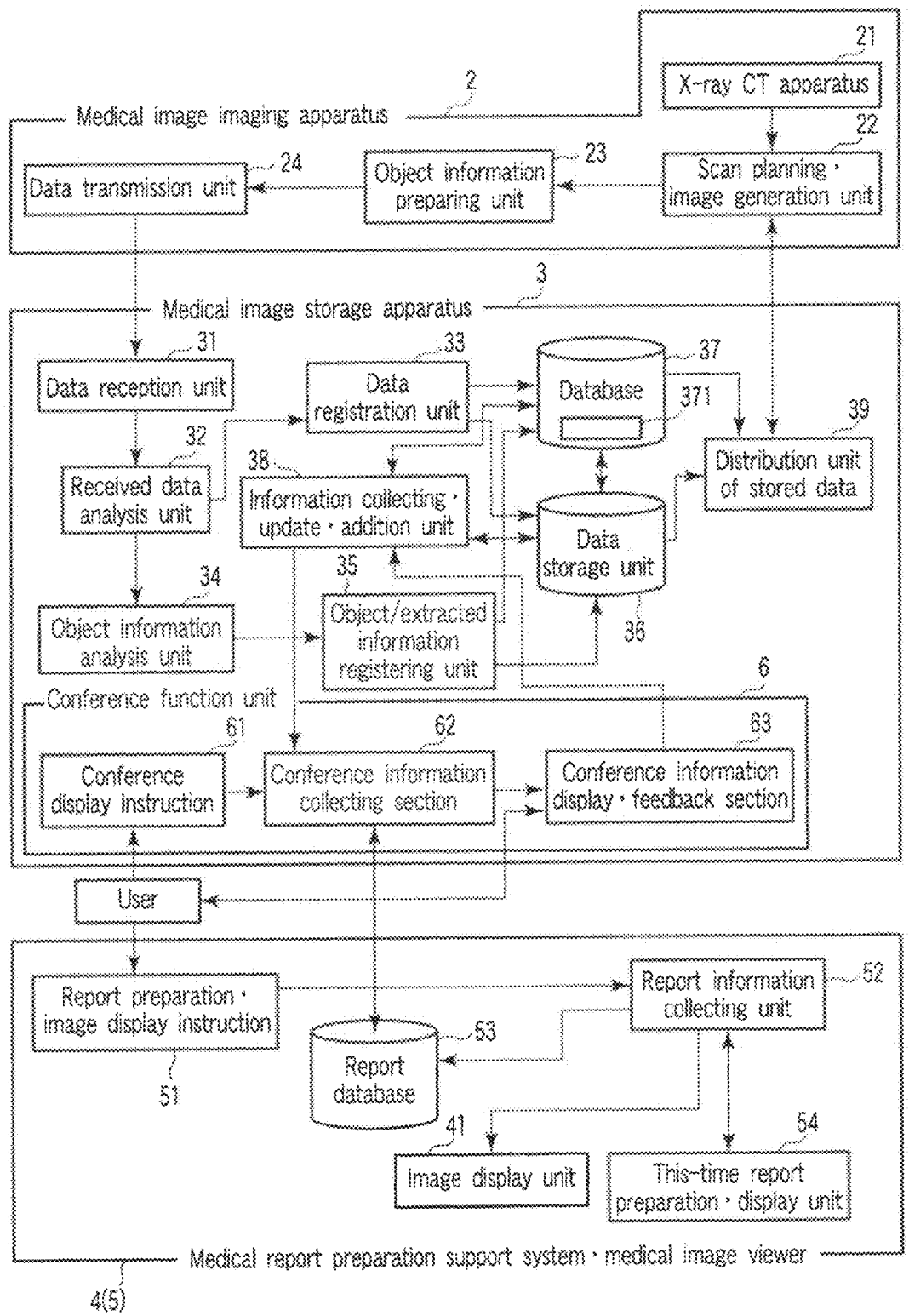
F I G. 2

| a Case name | b State (proceeding degree) | c Case information | d Report information | e Key image | f imaging range information |
|---|---|---|---|---|---|
| Tuberculosis | Considerably proceeding | 1. Age : 65 years<br>2. Gender : male<br>3. Diagnosis name : tuberculosis<br>4. Stage (before medication (before operation), after medication (after operation), hospitalization, hospital visit) : before medication<br>5. Length of stay in hospital : five days<br>6. Condition question information (medical history, family medical history, taste, medicine) : none<br>7. Treatment : medication<br>8. Treatment result : completely cured<br>9. Conference history information : none<br>10. Patient information (appropriately determine whether or not to disclose information) : name (NASU TARO), patient ID (555555), hospital facility (hospital A) | Report UID (information for searching or displaying concerned report) | Location value of image (file path, UID or the like) | Location value of image (file path, UID or the like) |
| | Not much proceeding | 18 years old<br>Male<br>Diagnosis name : tuberculosis<br>Stage : before medication<br>Length of stay in hospital : one day<br>Condition question information : none<br>Treatment : medication<br>Treatment result : completely cured<br>Conference history information :<br>Patient information : name (NASU TARO), patient ID (66666), hospital facility (hospital B) | Report UID (information for searching or displaying concerned report) | Location value of image (file path, UID or the like) | Location value of image (file path, UID or the like) |
| Stomach ulcer | | | | | |
| Pneumonia | | | | | |

| a Case name | b State (proceeding degree) | c Case information | d Report information | e Key image | f Imaging range information | g Evaluation of each item |
|---|---|---|---|---|---|---|
| Tuberculosis | Considerably proceeding | 1. Age : 65 years<br>2. Gender : male<br>3. Diagnosis name : tuberculosis<br>4. Stage (before medication (before operation), after medication (after operation), hospitalization, hospital visit) : before medication<br>5. Length of stay in hospital : five days<br>6. Condition question information (medical history, family medical history, taste, medicine) : none<br>7. Treatment : medication<br>8. Treatment result : completely cured<br>9. Conference history information : none<br>10. Patient information (appropriately determine whether or not to disclose information) : name (NASU TARO), patient ID (555555), hospital facility (hospital A)<br>... | Report UID (information for searching or displaying concerned report)<br>... | Location value of image (file path, UID or the like)<br>... | Location value of image (file path, UID or the like)<br>... | Case : 80%<br>State : 50%<br>Case information : 80% except 8, 100% in 8<br>Report information :<br>Key image : UID1, correction is necessary<br>UID2, no correction<br>Region, 100% |
| Stomach ulcer | ... | ... | ... | ... | ... | |
| Pneumonia | ... | ... | ... | ... | ... | |
| ... | | | | | | |

FIG. 11

| a | b | c | d | e | f | g |
|---|---|---|---|---|---|---|
| Case name | Purpose: (typical example/teaching, peculiar example), larger numeral indicates higher priority | Case information | Report information | Key image | Imaging range information | Evaluation of each item |
| Tuberculosis | Typical example: 1 | 1. Age: 65 years<br>2. Gender: male<br>3. Diagnosis name: tuberculosis<br>4. Stage (before medication (before operation), after medication (after operation), hospitalization, hospital visit): before medication<br>5. Length of stay in hospital: five days<br>6. Condition question information (medical history, family medical history, taste, medicine): none<br>7. Treatment: medication<br>8. Treatment result: completely cured<br>9. Conference history information: none<br>10. Patient information (appropriately determine whether or not to disclose information): name (NASU TARO), patient ID (555555), hospital facility (hospital A) | Report UID (information for searching or displaying concerned report) | Location value of image (file path, UID or the like) | Location value of image (file path, UID or the like) | Case: 80%<br>State: 50%<br>Case information: 80% except 8, 100% in 8<br>Report information: Key image: UID1, correction is necessary<br>UID2, no correction<br>Region, 100% |
|  | Teaching: 10 |  |  |  |  |  |
|  | Peculiar example: 30 | ... | ... | ... | ... | ... |
| Stomach ulcer |  | ... | ... | ... | ... | ... |
| Pneumonia |  | ... | ... | ... | ... | ... |
| ... |  |  |  |  |  |  |

IMAGE DIAGNOSIS SUPPORT SYSTEM AND IMAGE DIAGNOSIS SUPPORT METHOD

CROSS-REFERENCE TO RELATED APPLICATIONS

This application is based upon and claims the benefit of priority from prior Japanese Patent Application No. 2007-270325, filed Oct. 17, 2007, the entire contents of which are incorporated herein by reference.

BACKGROUND OF THE INVENTION

1. Field of the Invention

The present invention relates to an image diagnosis support system having a conference function, and an image diagnosis support method.

2. Description of the Related Art

Heretofore, as an image diagnosis support system, there has been a system in which a medical image acquired by a medical image imaging apparatus such as an X-ray CT apparatus or an ultrasonic diagnostic apparatus is stored together with imaging information and study information in a medical image storage apparatus, and this stored medical image is read by a medical image viewer to display the image in a monitor. The thus obtained monitor image is observed for diagnosis by a doctor, and this diagnosis result is then saved as a medical report.

Moreover, some of the recent image diagnosis support systems are each provided with a conference function of collecting various pieces of medical information such as the medical image stored together with the imaging information and the study information in the medical image storage apparatus and the diagnosis result saved as the medical report, and on the basis of the thus collected medical information, a plurality of doctors diagnose a patient to make a treatment plan through a conference.

In Jpn. Pat. Appln. KOKAI Publication No. 2005-43951, such a conference function is disclosed in which image data or medical information is selected and read from the image data or the medical information stored in an image data server or a hospital information system to display the same in the monitor or the like for use in the conference.

BRIEF SUMMARY OF THE INVENTION

However, in the disclosed conference function, stored image data or medical information is used for reference or investigation in a conference, but it is not considered that the result obtained by this conference is to be used in a subsequent conference, and there has been a problem that the image data or the medical information is not effectively utilized.

The present invention has been developed in view of the above situation, and an object thereof is to provide an image diagnosis support system having a conference function of realizing a more accurate conference by effective use of a medical image or object information used in a past conference.

According to an aspect of the present invention, there is provided an image diagnosis support system having a conference function, comprising an image storage unit which stores a medical image acquired by a medical image imaging unit; an information table storage unit which stores case information for each patient in correspondence with a case name and information of the medical image as an information table; a conference information collecting unit which collects the case information for each patient read from the information table storage unit in correspondence with the case name and the medical image read from the image storage unit in accordance with the information of the medical image of the information table, respectively, as conference information; a display unit which displays the collected conference information; an input unit which inputs a feedback index indicating a degree of evaluation as reference information concerning the displayed conference information; and a storage unit which associates the displayed conference information with the input feedback index and stores the same.

According to another aspect of the present invention, there is provided an image diagnosis support system having a conference function, comprising an image storage unit which stores a medical image acquired by a medical image imaging unit; an information table storage unit which stores case information for each patient in correspondence with a case name and information of the medical image as an information table; a conference information collecting unit which collects the case information for each patient read from the information table storage unit in correspondence with the case name and the medical image read from the image storage unit in accordance with the information of the medical image of the information table, respectively, as conference information; a display unit which displays information collected by the conference information collecting unit; and a feedback unit which feeds back the result of a conference based on contents displayed in this display unit to the information table.

According to another aspect of the present invention, there is provided an image diagnosis support method comprising collecting, from an image storage unit which stores a medical image acquired by a medical image imaging unit and an information table storage unit which stores case information for each patient in correspondence with a case name and information of the medical image as an information table, the case information for each patient read from the information table storage unit in correspondence with the case name and the medical image read from the image storage unit in accordance with the information of the medical image of the information table, respectively, as conference information; displaying the collected conference information; inputting a feedback index indicating a degree of evaluation or characteristics as reference information concerning the displayed conference information; performing addition, change and correction with respect to the displayed conference information in response to the input from a user; and feeding back the addition, the change and the correction performed with respect to the conference information to the information table stored in the information table storage unit, and associating the information table with the input feedback index to store the same.

BRIEF DESCRIPTION OF THE SEVERAL VIEWS OF THE DRAWING

FIG. 2 is a diagram for explaining the image diagnosis support system according to the first embodiment in more detail;

FIG. 3 is a diagram showing one example of a conference information table for use in the first embodiment;

FIG. 6 is a diagram showing one example of a search condition input window;

FIG. 7 is a diagram showing another example of the search condition input window;

FIG. 10 is a diagram showing one example of a feedback index input concerning conference information shown in FIG. 9;

FIG. 11 is a diagram showing one example of the changed conference information table;

FIG. 12 is a diagram showing another example of the changed conference information table; and FIG. 13 is a diagram showing one example of the search condition input window in which the feedback index is included in search conditions.

DETAILED DESCRIPTION OF THE INVENTION

Hereinafter, embodiments of the present invention will be described with reference to the drawings.

(First Embodiment)

Figure 1:
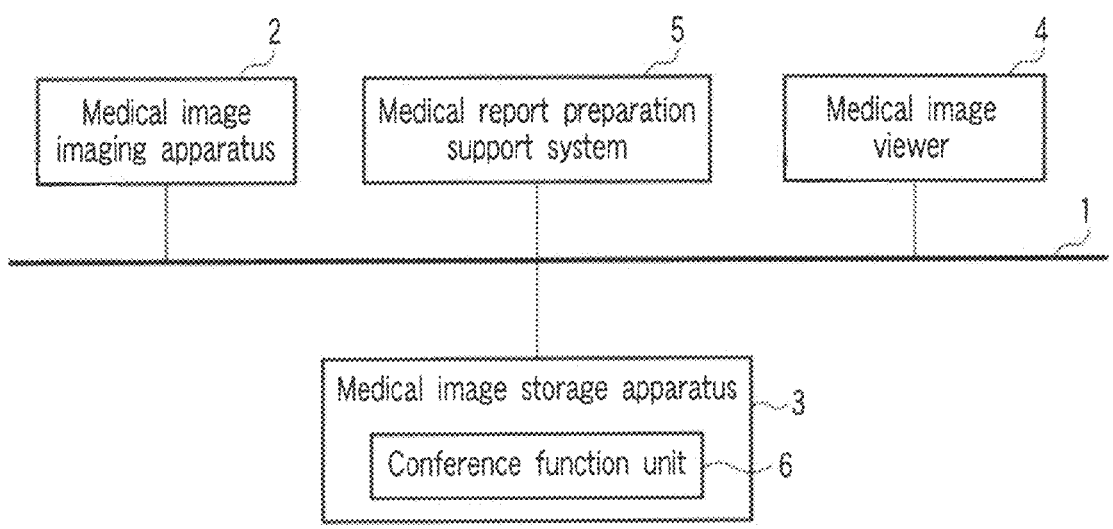
FIG. 1 is a diagram showing a schematic constitution of an image diagnosis support system according to a first embodiment of the present invention.

FIG. 1 shows a schematic constitution of an image diagnosis support system according to a first embodiment of the present invention. In FIG. 1, reference numeral 1 is a network such as an LAN, and this network 1 is connected to a medical image imaging apparatus 2, a medical image storage apparatus 3, a medical image viewer 4 and a medical report preparation support system 5. In this case, the medical image viewer 4 and the medical report preparation support system 5 are incorporated in the same apparatus.

The medical image imaging apparatus 2 has an X-ray CT apparatus, an ultrasonic diagnostic apparatus and the like, and generates a medical image collected from a patient's diagnosis part. Moreover, the medical image imaging apparatus prepares and generates patient information on the medical image, imaging information (imaging conditions, a imaging range, etc.), key image information, past study information referred to and the like as object information (medical information). The medical image storage apparatus 3 stores and manages the medical image and the object information generated by the medical image imaging apparatus 2. This medical image storage apparatus 3 is provided with a conference function unit 6. This conference function unit 6 will be described later. The medical image viewer 4 has a TV monitor (not shown) and the like, and reads the medical image and medical information stored in the medical image storage apparatus 3 to display the same. The medical report preparation support system 5 supports the preparation of a medical report based on a result obtained by observing and diagnosing the TV monitor image of the medical image viewer 4 by a doctor, and the system stores the medical report prepared here.

FIG. 2 is a diagram for explaining the medical image imaging apparatus 2, the medical image storage apparatus 3, the medical image viewer 4 and the medical report preparation support system 5 constituting the image diagnosis support system in more detail.

The medical image imaging apparatus 2 has an X-ray CT apparatus 21 as a medical image imaging unit, a scan planning•image generation unit 22, an object information preparing unit 23 and a data transmission unit 24. The X-ray CT apparatus 21 scans and radiates an X-ray to a patient's diagnosis part, and detects a transmitted X-ray quantity distribution of the part to generate a tomographic image as the medical image. The scan planning•image generation unit 22 takes information used in the past inspection of the same patient from the medical image storage apparatus 3 (a stored data distribution unit 39), instructs a user to make and perform a scan plan with respect to the X-ray CT apparatus 21 based on this information, and allows the X-ray CT apparatus 21 to generate the tomographic image based on this scan plan. The object information preparing unit 23 prepares and generates the patient information concerned with the medical image, the imaging information (the imaging conditions, the imaging range, etc.), the key image information indicating the characteristics of the diagnosed part, the past study information referred to during the imaging and the like as object information together with the medical image acquired by the X-ray CT apparatus 21. The data transmission unit 24 transmits the medical image and the object information output from the object information preparing unit 23 to the medical image storage apparatus 3 via the network 1.

The medical image storage apparatus 3 has a data reception unit 31, a received data analysis unit 32, a data registration unit 33, an object information analysis unit 34, an object information•extracted information registering unit 35, a data storage unit 36, a database 37, an information collecting•update•addition unit 38 and the stored data distribution unit 39. The data reception unit 31 performs reception processing of the medical image and the object information input from the medical image imaging apparatus 2. The received data analysis unit 32 analyzes the contents received by the data reception unit 31 to judge whether the contents are the object information or usual digital imaging and communication in medicine (DICOM) data. The data registration unit 33 registers the medical image other than the object information output from the received data analysis unit 32 in the database 37. The object information analysis unit 34 extracts necessary information from the object information output from the received data analysis unit 32. The object information•extracted information registering unit 35 appropriately registers the information extracted from the object information in the data storage unit 36 as an image storage unit and the database 37. On receiving the medical image and the object information from the data registration unit 33 and the object information•extracted information registering unit 35, the data storage unit 36 writes and stores the same in an appropriate plate. In this case, when the storage place of the medical image or the object information is determined, deleted or changed, the data storage unit performs communication with the database 37 to correct the database 37. This data storage unit 36 may be a hard disk (HDD) or a network attached storage (NAS) provided in another place. The database 37 has an information table 371 as an information table storage unit. This information table 371 manages case information for each patient extracted from the object information, the information (search information or imaging information) of the medical image and the like in correspondence with each case name. It is to be noted that the information table 371 of the information table storage unit may be the same storage unit as the above image storage unit (the data storage unit 36).

FIG. 3 shows one example of the information table 371. The table has items such as a case name column a, a state (proceeding degree) column b, a case information column c, a report information column d, a key image column e and a imaging range information column f. Here, a case name such as "tuberculosis" or "stomach ulcer" is written in the medical condition column a, and a state (a proceeding degree) such as "considerably proceeding" or "not much proceeding" is written for each case in the state (proceeding degree) column b. Moreover, "age", "gender", "stage", "length of stay in hospital" and the like are written for each case name in correspondence with the state (the proceeding degree) "considerably proceeding" in the case information column c, and similarly "age", "gender", "stage", "length of stay in hospital" and the like are written as the patient information in correspondence with "not much proceeding". In the report information column d, report individual identification information (UID) for searching or displaying a concerned report written in a report database 53 described later is written for each state (proceeding degree) of each case name. Moreover, in the key image column e, key image information (the location of the image (a file path, the individual identification information (UID) or the like) to be acquired from the object information is written as the search information of the medical image for each state (proceeding degree) of each case name. Similarly, in the imaging range information column f, the imaging information (coordinate information on the image, the size of a range or the like) of the medical image to be acquired from the object information is written for each state (proceeding degree) of each case name. Here, medical condition information to be written in the medical condition information column c is also collected from a hospital information system (not shown) via a network in addition to the data storage unit 36 and the database 37.

The information collecting•update•addition unit 38 provides the information to the conference function unit 6 described later, and performs change such as the update or addition of the data storage unit 36 and the database 37 (the information table 371) in accordance with feedback information during the conference. In response to a request from the outside, the stored data distribution unit 39 reads information (the medical image, the object information or the like) corresponding to the request, from the data storage unit 36 and the database 37, to distribute the same to a requester (in this case, the data storage unit 36 and the requester sometimes directly exchange the medical image).

The medical image viewer 4 has an image display unit 41 such as a TV monitor, and the medical report preparation support system 5 has a report preparation•image display instruction unit 51, a report information collecting unit 52, the report database 53 and a this-time report preparation•display unit 54. The image display unit 41 displays an image for observation in accordance with the information collected by the report information collecting unit 52. The report preparation•image display instruction unit 51 instructs preparation for the generation of the report of a designated inspection, and image display. The report information collecting unit 52 collects the concerned information necessary for preparing the report from the report database 53, and collects information for the image display from the data storage unit 36 and the database 37. Moreover, the prepared report information (diagnosis result or the like) is stored in the report database 53, and is transmitted to the data storage unit 36 via the stored data distribution unit 39. The report database 53 stores the concerned information necessary for preparing the report and the prepared report information. The this-time report preparation•display unit 54 displays the observation image together with a report generation preparatory screen based on the information collected by the report information collecting unit 52, and prepares the medical report by the report preparation support. Moreover, the prepared this-time medical report is returned to the report information collecting unit 52.

On the other hand, the medical image storage apparatus 3 is provided with the conference function unit 6. This conference function unit 6 has a conference display instructing section 61, a conference information collecting section 62, and a conference information display•feedback section 63. The conference display instructing section 61 instructs, for example, the display of the conference corresponding to the case name in response to a user's request. The conference information collecting section 62 collects information concerned with the conference. In this case, the conference information collecting section 62 reads and collects the information of the conference from the data storage unit 36, the database 37 (the information table 371), the report database 53 and the like.

The conference information display•feedback section 63 displays the information collected by the conference information collecting section 62 in a display unit (not shown) such as the TV monitor. Moreover, the section waits for the input (performed by the user) of the result (a radiogram interpretation result, correction of imaging conditions, evaluation with respect to the case or the like) of the conference based on this displayed information, and feeds back this input information to the information collecting•update•addition unit 38 to perform the update, the addition or the like of the contents of the information table 371 (FIGS. 11 and 12 show one example of the changed information table 371). In this case, the display unit may be provided outside the conference information display•feedback section 63.

Next, an operation of the embodiment having such a constitution will be described.

First, in the medical image imaging apparatus 2, when the tomographic image of the patient's diagnosis part is photographed by the X-ray CT apparatus 21, together with the medical image, the patient information concerned with this medical image, the imaging information (the imaging conditions, the imaging range or the like), the key image information indicating the characteristics of the diagnosis part, the past study information referred to and the like are generated as the object information by the object information preparing unit 23, and are sent to the medical image storage apparatus 3 via the network 1.

In the medical image storage apparatus 3, the data registration unit 33 registers the medical image in the database 37, and the necessary information of the object information extracted by the object information•extracted information registering unit 35 is registered in the data storage unit 36 and the database 37 (the information table 371). Afterward, when the report preparation•image display instruction unit 51 of the medical report preparation support system 5 instructs the preparation for the report generation and the image display, the report information collecting unit 52 collects the concerned information necessary for preparing the report from the report database 53, and the information necessary for displaying the observation image is collected from the data storage unit 36 and the database 37. The collected information is displayed as the observation image together with the report generation preparatory screen in the image display unit 41. Then, on the screen of the image display unit 41, the medical report is prepared by the report preparation support based on the doctor's diagnosis result, and this prepared medical report is stored in the report database 53.

Figure 4:
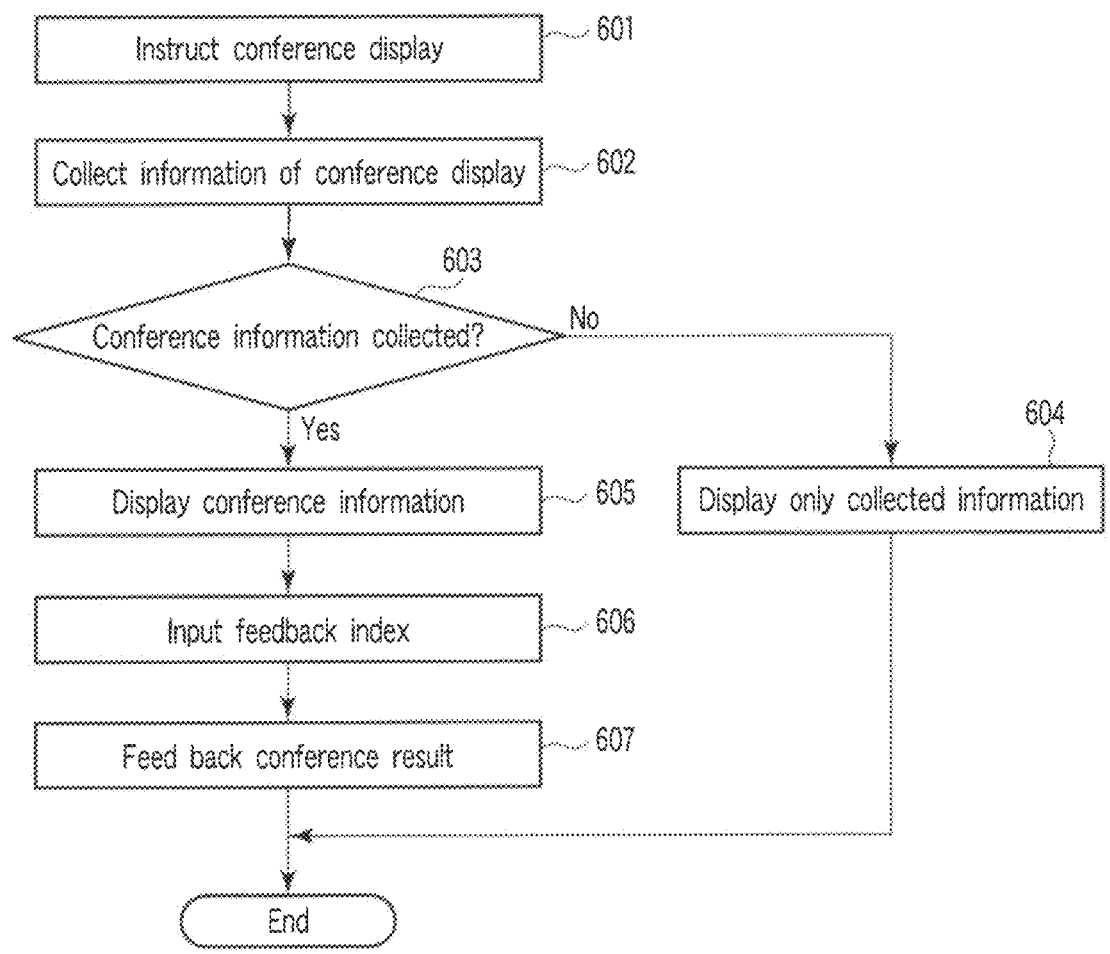
FIG. 4 is a flow chart for explaining an operation of the first embodiment.

Next, when the conference is executed, a flow chart shown in FIG. 4 is executed.

Figure 5:
FIG. 5 is a diagram showing one example of a conference information acquisition screen.

First, in response to a predetermined operation, for example, a conference information acquisition screen shown in FIG. 5 is displayed in the display unit of the medical image storage apparatus 3. In the displayed acquisition screen, for example, a concerned information search button can be clicked to open a search condition input window shown in FIG. 6. In the search condition input window, for example, title "test 2" of doctor in charge "TOSHIBA ICHIRO" can be clicked to automatically input condition contents concerning the test 2 with respect to various condition items such as "case name", "stage", "length of stay in hospital", "gender" and "age". After the input, when an "OK" button is clicked, a conference display instruction from the user is input. In response to the instruction from the user, the conference display instructing section 61 outputs an instruction for conference display to the conference information collecting section 62 (step 601).

Figure 6:
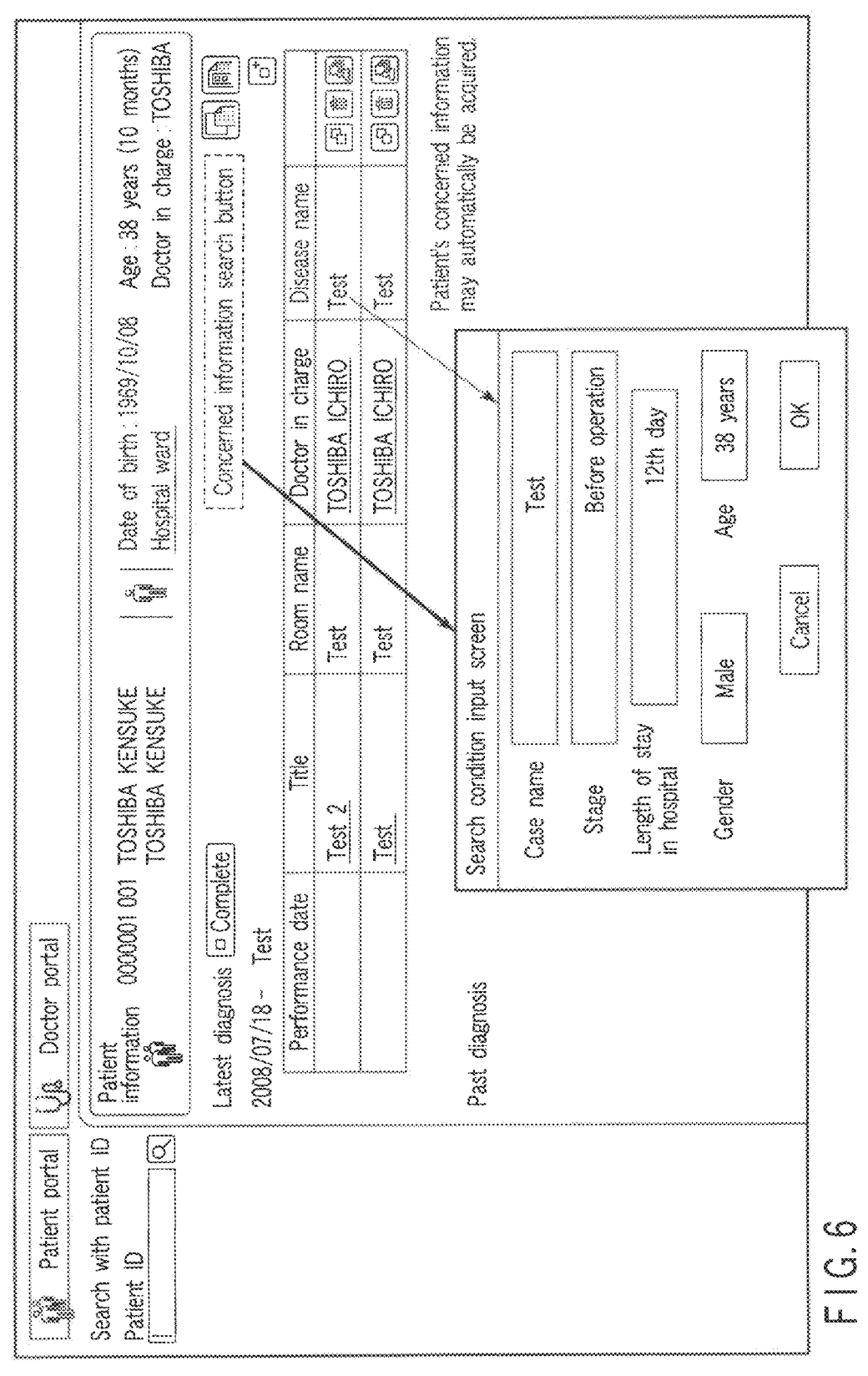
Figure 7:
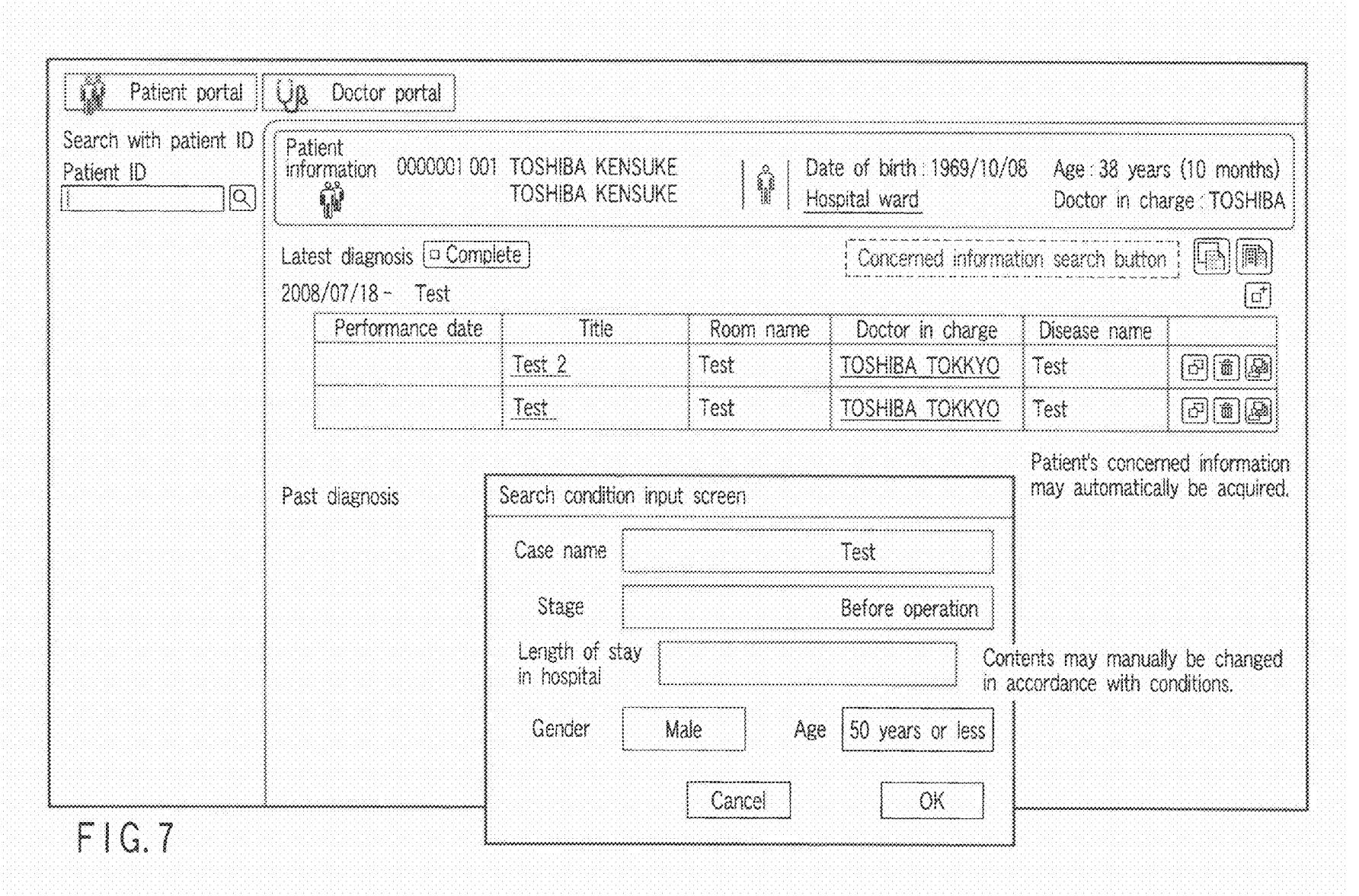

It is to be noted that the search conditions to be displayed in the search condition input window are not limited to the example of FIG. 6, and various conditions can be added or decreased by setting. Moreover, as shown in FIG. 7, a desired search condition item ("length of stay in hospital" in the example of FIG. 7) may be selected to manually input condition contents.

Next, in response to the instruction for the conference display, the conference information collecting section 62 collects the conference display information matching the input search conditions from the data storage unit 36, the database 37 (the information table 371) and the report database 53 (step 602). In this case, as shown in FIG. 3, the information table 371 has items such as the case name column a, the state (proceeding degree) column b, the case information column c, the report information column d, the key image column e and the imaging range information column f. The information of the state (proceeding degree) column b, the case information column c, the report information column d, the key image column e and the imaging range information column f corresponding to the case name designated in the case name column a is collected as the information of the conference display.

Next, the conference information collecting section 62 judges whether or not the information of the conference display has been collected, that is, whether or not the collected information is the information of the conference display corresponding to the designated case name (step 603). Here, if it is judged that the answer to the step is NO, the conference information display•feedback section 63 displays the information collected by the conference information collecting section 62 in the TV monitor (not shown) or the like (step 604).

Figure 8:
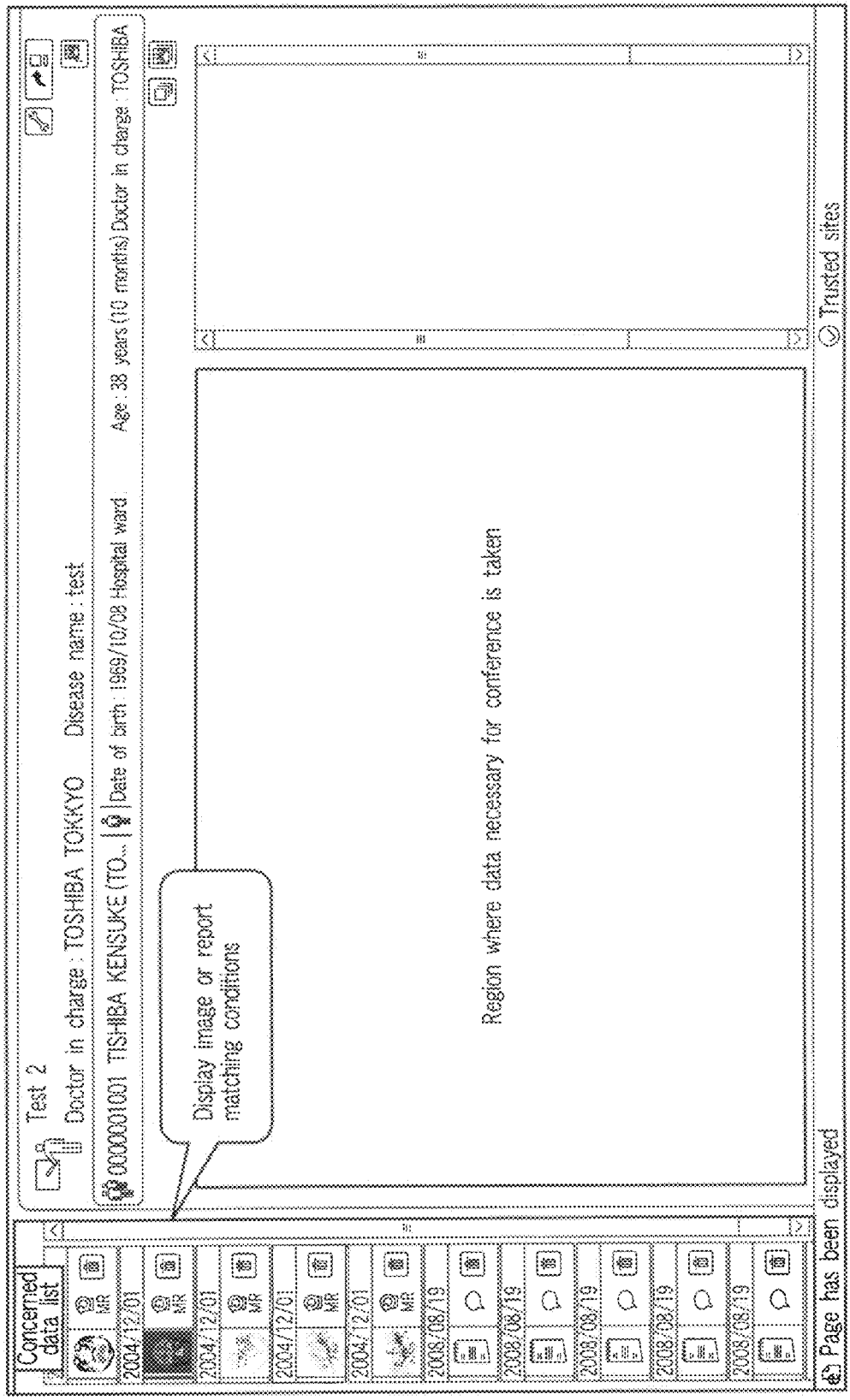
FIG. 8 is a diagram showing one example of a display configuration of information collected by a conference information collecting section 62.

On the other hand, in a case where it is judged that the answer to the step 603 is YES, the conference information display•feedback section 63 displays the conference information in the TV monitor (step 605). That is, the conference information display•feedback section 63 displays a list of the information collected by the conference information collecting section 62 on the left side of a screen shown in, for example, FIG. 8. Moreover, in the conference information display•feedback section 63, the information selected from the displayed list of conference information by the drag and drop operation as shown in, for example, FIG. 9 by the user is displayed as the conference information in a specific configuration. For example, a plurality of doctors perform a conference with reference to the conference information displayed in the display section in this manner.

Next, the feedback index concerning the displayed conference information is input via an input unit (step 606). Here, the feedback index is a value or information indicating the feedback degree of the conference information for reference in a future conference. This feedback index is input for each item via the input unit by the user.

Figure 9:
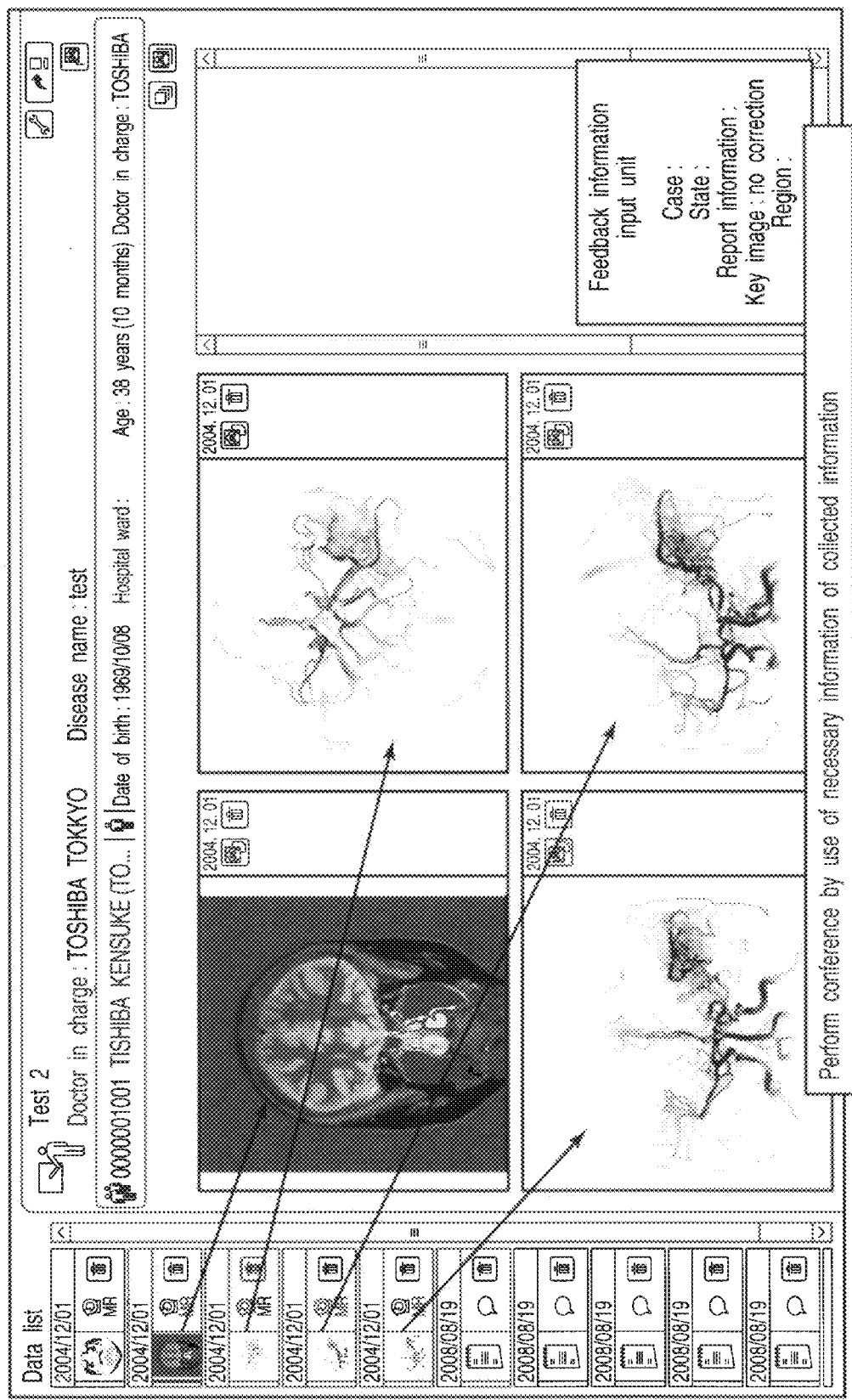
FIG. 9 is a diagram showing one example of a display configuration of information selected by a drag and drop operation in a screen of FIG. 8.
Figure 10:
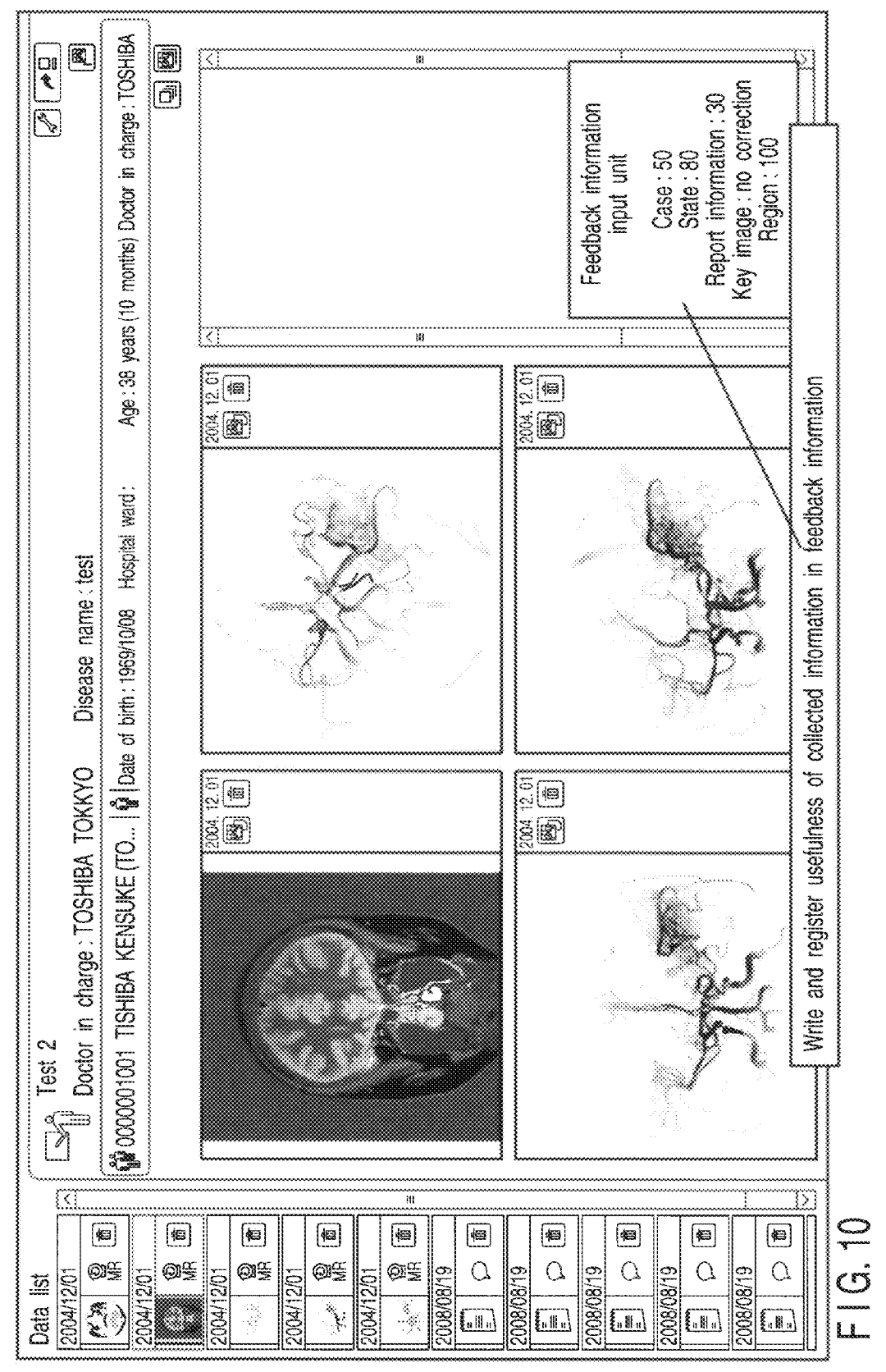

FIG. 10 is a diagram showing one example of the feedback index input concerning the conference information shown in FIG. 9. In the drawing, the feedback index in a case where the conference information is surely referred to in future is set to 100%, evaluation values are input as the feedback indexes in items such as "case", "state", "report information" and "region", and the presence of correction is input as the feedback index in the "key image".

It is to be noted that the feedback index is not limited to the example of FIG. 10. For example, ranking "A, B and C", case characteristics "typical, non-typical" and the like are displayed.

Next, the conference information display•feedback section 63 transmits, to the information collecting•update•addition unit 38, the conference result including the feedback index, the radiogram interpretation result, the correction of the imaging conditions, the evaluation with respect to the case and the like for each input item. The information collecting•update•addition unit 38 performs change such as the update or the addition of the contents of the database 37 (the information table 371) to execute the feedback of the conference result (step 607).

FIG. 11 shows one example of the changed conference information table 371. In this case, an item of an evaluation column g is added to the items of the case name column a, the state (proceeding degree) column b, the conference information, the report information column d, the key image column e and the imaging range information column f. In this evaluation column g, evaluation based on the conference result is additionally written with respect to the contents of the items of the case name column a, the state (proceeding degree) column b, the conference information, the report information column d, the key image column e and the imaging range information column f.

Next, when the conference is executed again and the instruction for the conference display corresponding to the case name is output in response to the user's request in the same manner as described above, the flow chart shown in FIG. 4 is executed to collect the information of the conference display. In this case, the information of the conference display is collected based on the contents of the changed information table 371 shown in FIG. 11, and the conference display information collected here is displayed in the TV monitor or the like. Then, while referring to the information displayed in the TV monitor, the doctors perform the conference, and the result of the conference is fed back to the information collecting•update•addition unit 38 by the conference information display•feedback section 63. In consequence, the information collecting•update•addition unit 38 further adds the contents of the data storage unit 36 and the database 37 (the information table 371).

FIG. 12 is a diagram showing another example of the changed information table 371. In this case, among the case name column a, the state (proceeding degree) column b, the case information column c, the report information column d, the key image column e, the imaging range information column f and the evaluation column g, instead of the state (proceeding degree) column b, an item of a purpose column h is added. In this purpose column h, as the conference result, information classified for each purpose, for example, a typical example, teaching, a peculiar example or the like is written for each case name.

Subsequently, when the conference is similarly executed, the information of the conference display is collected based on the contents of the information table 371, and displayed in the TV monitor. Then, while referring to this displayed conference information, the conference is performed, and this conference result is fed back by the conference information display•feedback section 63. Furthermore, the contents of the information table 371 are updated in preparation for the next collection of the information of the conference display.

Therefore, in this case, the medical image is acquired by the medical image imaging apparatus 2, the object information on the medical image is generated, and the medical image and the object information on the medical image are stored in the data storage unit 36 and the database 37. Moreover, the case information corresponding to the case name based on the object information for each patient and the information of the medical image are stored in the information table 371. The case information for each patient read from the information table 371 corresponding to the case name in accordance with the conference instruction, and the medical image read in accordance with the information of the medical image of the information table 371 are collected as the conference information. The conference display of the collected information is performed. Moreover, the conference result based on the displayed contents is fed back to the information table 371 by the conference information display•feedback section 63 to change the contents. In consequence, the case information and the medical image for each patient based on the object information used in the past conference are effectively used in the reference or the investigation during the conference. Furthermore, the result obtained by this conference is fed back to the information table 371, and reflected as a judgment material such as a diagnosis course for the next conference, so that the object information and the medical image used in the past conference can repeatedly effectively be used. Moreover, since the case information and the medical image corresponding to the case name are collected as the information of the conference display based on the information table 371 changed in accordance with the conference result, the plurality of doctors can diagnose the patient and determine the diagnosis plan by the conference based on the latest conference information to be updated, so that precise conference can be realized.

(Second Embodiment)

Next, a second embodiment of the present invention will be described. In the present embodiment, the searching of conference information by use of a feedback index will be described.

Figure 13:
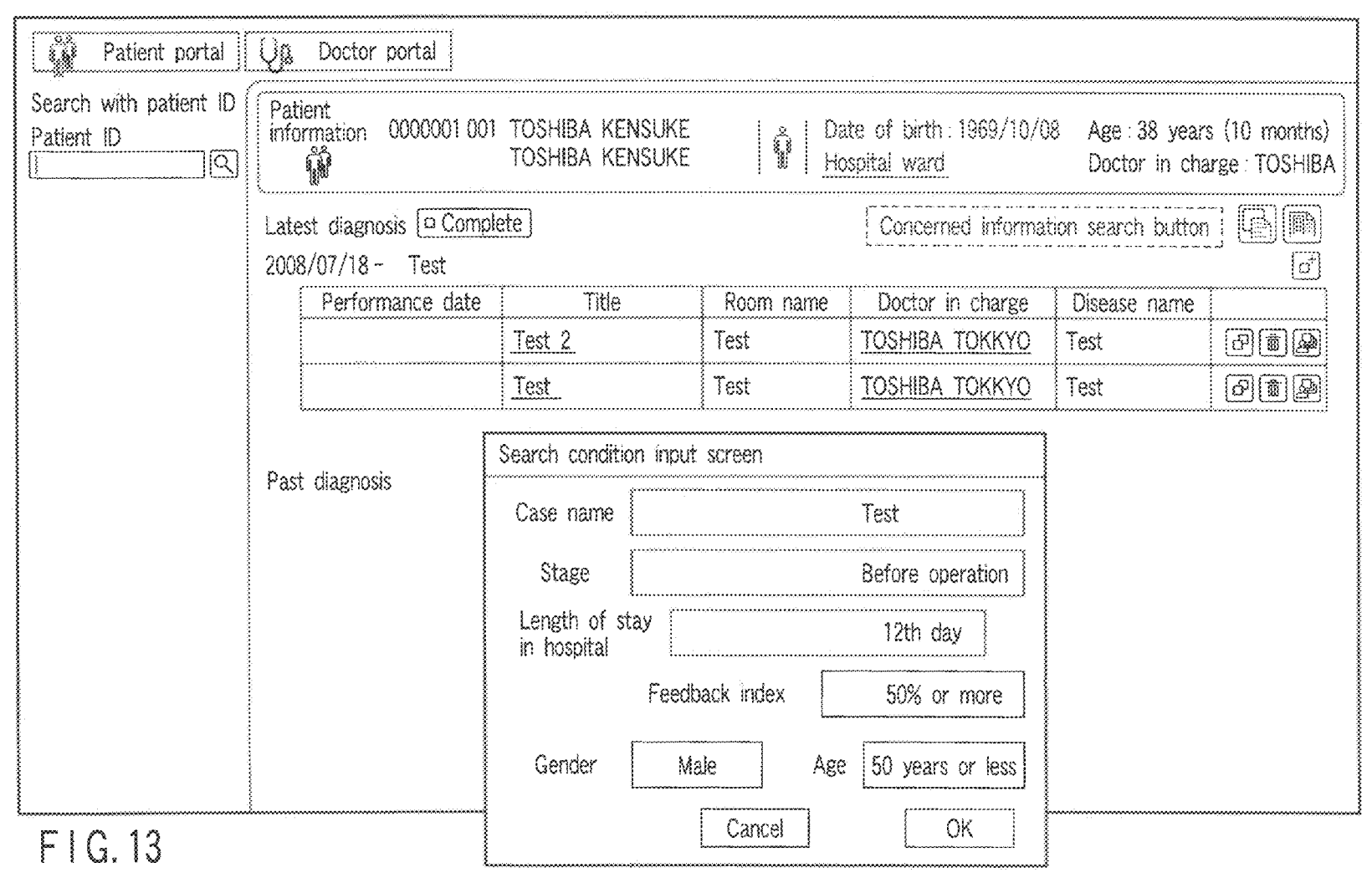

In the present embodiment, for example, in step 601 of instructing conference display in FIG. 4, a conference information acquisition screen and a search condition input window shown in, for example, FIG. 13 are displayed. In this search condition input window, a new search condition item "the feedback index" is added as compared with, for example, the examples shown in FIGS. 6, 7. A user can input an index indicating desired conditions concerning the feedback index via an input unit (in the example of FIG. 13, "50% or more" is input) and can click a button to instruct the conference display. In consequence, the information of the conference display in which the feedback index is set to 50% or more is collected from a data storage unit 36, a database 37 (an information table 371) and a report database 53.

It is to be noted that FIG. 13 shows an example in which "50%" or more is input as the search condition contents of "the feedback index". However, "the feedback index" is not limited to the example. For example, the feedback index concerning a specific search condition item, for example, "case 80% or more" may be input. Furthermore, instead of a numeric value, the feedback index indicating a state or characteristics, for example, "typical" or "non-typical" may be input.

The above embodiments include various stages of inventions, and various inventions can be extracted by appropriately combining a plurality of disclosed constitutional requirements.

For example, in the above embodiments, the information specifying the patient is displayed in the conference display, but the specific information on the patient is sometimes not to be disclosed. In this case, needless to say, the patient information does not have to be displayed. In addition, the present invention is not limited to the above embodiments, and can variously be modified without departing from the scope of the invention.

Furthermore, even in a case where several constitutional requirements are deleted from all the constitutional requirements described in the embodiments, when the problem described in the paragraphs of the problem to be solved by the invention can be solved and the effect described in the paragraphs of the effect of the invention is obtained, a constitution from which the constitutional requirements have been deleted can be extracted as the invention.

What is claimed is:

1. An image diagnosis support system having a conference function, comprising:
   an image storage unit which stores a medical image acquired by a medical image imaging unit;
   an information table storage unit which stores case information for each patient in correspondence with a case name and information of the medical image as an information table;
   a conference information collecting unit which collects the case information for each patient read from the information table storage unit and the medical image read from the image storage unit in accordance with the information table to generate conference information;
   a display unit which displays the conference information;
   an input unit which inputs addition, change, correction, and a feedback index, the addition, change, and correction concerning the displayed conference information, and the feedback index indicating a degree of priority with respect to collecting the case information for each patient, and which is utilized in a future conference; and
   a feedback unit which updates the information table for the future conference in accordance with the addition, the change, the correction, and the feedback index to feedback a conference result on the basis of the displayed conference information; and
   wherein the conference information collecting unit collects the case information and the medical image in accordance with the updated information table.

2. The image diagnosis support system according to claim 1, wherein the information of the medical image of the information table is at least one of search information and imaging information of the medical image.

3. The image diagnosis support system according to claim 1, wherein the feedback unit is configured to add evaluation information based on a conference result to each case name of the information table.

4. The image diagnosis support system according to claim 1, wherein the feedback unit is configured to add information classified for each purpose based on a conference result to each case name.

5. The image diagnosis support system according to claim 1, wherein the image storage unit stores object information on the medical image acquired by the medical image imaging unit, and case information for each patient is based on the object information.

6. The image diagnosis support system according to claim 5, wherein the object information is at least one of patient information, imaging information, key image information indicating the characteristics of a diagnosis part and past study information referred to during imaging.

7. The image diagnosis support system according to claim 1, wherein the conference information collecting unit collects the conference information by use of search conditions including the feedback index.

8. An image diagnosis support system having a conference function comprising:
  an image storage unit which stores a medical image acquired by a medical image imaging unit;
  an information table storage unit which stores case information for each patient in correspondence with a case name and information of the medical image as an information table;
  a conference information collecting unit which collects the case information for each patient read from the information table storage unit and the medical image read from the image storage unit in accordance with the information table to generate conference information;
  a display unit which displays the conference information; and
  a feedback unit which updates the information table to be utilized in a future conference to feed back a result of a conference based on contents displayed in the display unit; and
  wherein the conference information collecting unit collects the case information and the medical image in accordance with the updated information table.

9. The image diagnosis support system according to claim 8, wherein the information of the medical image of the information table is at least one of search information and imaging information of the medical image.

10. The image diagnosis support system according to claim 8, wherein the feedback unit is configured to add evaluation information based on the conference result to each case name of the information table.

11. The image diagnosis support system according to claim 8, wherein the feedback unit is configured to add information classified for each purpose based on the conference result to each case name.

12. The image diagnosis support system according to claim 8, wherein the image storage unit stores object information on the medical image acquired by the medical image imaging unit, and case information for each patient is based on the object information.

13. The image diagnosis support system according to claim 12, wherein the object information is at least one of patient information, imaging information, key image information indicating the characteristics of a diagnosis part and past study information referred to during imaging.

14. An image diagnosis support method comprising:
  collecting, from an image storage unit which stores a medical image acquired by a medical image imaging unit and an information table storage unit which stores case information for each patient in correspondence with a case name and information of the medical image as an information table, the case information for each patient read from the information table storage unit in correspondence with the case name and the medical image read from the image storage unit in accordance with the information of the medical image of the information table, respectively, as conference information;
  displaying the collected conference information;
  inputting a feedback index indicating a degree of priority with respect to collecting the case information for each patient, and which is utilized in a future conference;
  performing addition, change and correction with respect to the displayed conference information in response to the input from a user; and
  feeding back the addition, the change and the correction performed with respect to the conference information to the information table stored in the information table storage unit, and associating the information table with the input feedback index to store the same for the future conference; and
  wherein the conference information collecting collects the case information and the medical image in accordance with the updated information table.

15. The image diagnosis support method according to claim 14, wherein the information of the medical image of the information table is at least one of search information and imaging information of the medical image.

16. The image diagnosis support method according to claim 14, wherein the feedback permits adding evaluation information based on a conference result to each case name of the information table.

17. The image diagnosis support method according to claim 14, wherein the feedback permits adding information classified for each purpose based on a conference result to each case name.

18. The image diagnosis support method according to claim 14, wherein the image storage unit stores object information on the medical image acquired by the medical image imaging unit, and case information for each patient is based on the object information.

19. The image diagnosis support method according to claim 18, wherein the object information is at least one of patient information, imaging information, key image information indicating the characteristics of a diagnosis part and past study information referred to during imaging.

20. The image diagnosis support method according to claim 14, wherein the collection of the conference information collects the conference information by use of search conditions including the feedback index.

21. The image diagnosis support system according to claim 1, wherein the conference information collects the case information and the medical image on the basis of the updated information table.

22. The image diagnosis support system according to claim 8, wherein the conference information collects the case information and the medical image on the basis of the updated information table.

* * * * *